United States Patent
Won et al.

(10) Patent No.: US 11,434,135 B2
(45) Date of Patent: Sep. 6, 2022

(54) GRAPHITE SHEET HAVING EXCELLENT THERMAL CONDUCTIVITY AND METHOD FOR PREPARING THE SAME

(71) Applicant: PI Advanced Materials Co., Ltd., Chungcheongbuk-do (KR)

(72) Inventors: Dong Young Won, Seoul (KR); Hyun Jai Lim, Gumi-si (KR); Kyung Su Kim, Seoul (KR)

(73) Assignee: PI Advanced Materials Co., Ltd., Chungcheongbuk-do (KR)

(*) Notice: Subject to any disclaimer, the term of this patent is extended or adjusted under 35 U.S.C. 154(b) by 41 days.

(21) Appl. No.: 16/944,029

(22) Filed: Jul. 30, 2020

(65) Prior Publication Data

US 2020/0361776 A1    Nov. 19, 2020

Related U.S. Application Data

(62) Division of application No. 15/858,604, filed on Dec. 29, 2017, now Pat. No. 10,766,773.

(30) Foreign Application Priority Data

Nov. 10, 2017   (KR) .................. 10-2017-0149916

(51) Int. Cl.
*C07C 233/00* (2006.01)
*C01B 32/205* (2017.01)

(52) U.S. Cl.
CPC .......... *C01B 32/205* (2017.08); *C07C 233/00* (2013.01); *C01B 2204/04* (2013.01); *C01B 2204/24* (2013.01); *C01P 2006/32* (2013.01)

(58) Field of Classification Search
CPC .................................................. C09C 233/00
See application file for complete search history.

(56) References Cited

U.S. PATENT DOCUMENTS

| | | | |
|---|---|---|---|
| 5,993,661 A * | 11/1999 | Ruckenstein | B01D 39/1676 210/231 |
| 8,366,979 B2 | 2/2013 | Dai et al. | |
| 8,440,315 B2 * | 5/2013 | Carney | C09J 7/25 428/473.5 |
| 8,865,111 B2 | 10/2014 | Nishikawa et al. | |

FOREIGN PATENT DOCUMENTS

| | | |
|---|---|---|
| CN | 105967170 A | 9/2016 |
| CN | 106744792 A | 5/2017 |
| CN | 108300278 A | 7/2018 |
| JP | 6-145378 A | 5/1994 |
| JP | 2006-225640 A | 8/2006 |
| JP | 2008-213872 A | 9/2008 |
| JP | 5089047 B2 | 12/2012 |
| JP | 2016-17169 A | 2/2016 |
| JP | 2017-43668 A | 3/2017 |
| JP | 6735542 B2 | 8/2020 |
| KR | 10-2017-0112329 A | 10/2017 |

OTHER PUBLICATIONS

Notice of Reasons for Rejection, dated Oct. 20, 2018, for Korean Application No. 10-2017-0149916, 16 pages. (w/ Machine Generated English Translation).
Office Action, dated Apr. 14, 2021, for Taiwan Patent Application No. 11020341150, 19 pages. (w /English Translation).
Notice of Allowance (w /English Translation), dated May 6, 2022, for Chinese Patent Application No. 201810083051.3, (7 pages).
Notice of Allowance, dated Jul. 12, 2022, for Japanese Patent Application No. 2017-249200. (4 pages).

* cited by examiner

*Primary Examiner* — Stuart L Hendrickson
(74) *Attorney, Agent, or Firm* — Seed IP Law Group LLP

(57) ABSTRACT

The present invention provides a method for preparing a high-performance graphite sheet by imidizing a polyamic acid resulting from a reaction of dianhydride monomer(s) and diamine monomer(s) to obtain a polyimide film; and carbonizing and/or graphitizing the polyimide film to obtain a high-performance graphite sheet, where the polyimide film contains 2 or more fillers having different average particle diameters, and the thermal conductivity of the graphite sheet is at least 1,400 W/m·K. Further, the present invention provides a graphite sheet obtained by the above method.

9 Claims, 2 Drawing Sheets

GRAPHITE SHEET HAVING EXCELLENT THERMAL CONDUCTIVITY AND METHOD FOR PREPARING THE SAME

CROSS-REFERENCE TO RELATED APPLICATIONS

This application is a divisional application of U.S. application Ser. No. 15/858,604, filed Dec. 29, 2017 (now allowed), which claims the benefit under 35 U.S.C. § 119 (d) of Korean Patent Application No. 10-2017-0149916, filed Nov. 10, 2017, which applications are incorporated herein by reference in their entirety.

FIELD OF THE INVENTION

The present invention is directed to a high-performance graphite sheet and a method for preparing the same.

BACKGROUND OF THE INVENTION

In general, a polyimide resin denotes a high heat-resistant resin, which is prepared by solution-polymerizing an aromatic dianhydride(s), and an aromatic diamine(s) or diisocyanate(s) to obtain a polyamic acid derivative, and ring-closure dehydrating and imidizing the polyamic acid derivatives at high temperature to obtain the high heat-resistant resin.

A polyimide film denotes a film prepared in a thin layer from the polyimide resin. Since the polyimide film has an excellent mechanical and thermal dimensional stability and a chemical stability, it is widely used in an electronic/electric material application, space/aviation application, and telecommunication application.

Particularly, a current trend for an electronic device tends to be light-weight, miniaturized, thin and highly-integrated. This trend results in an increase of heat generation per unit volume, followed by problems resulting from such heat loading. Therefore, an effective heat dissipation of such electronic device is important.

In this regard, graphite is exemplified as a means for heat-dissipation used in such electronic device. Graphite has a graphene-stacking structure, wherein the graphene is a 2-dimensional sheet consisting of a plate of carbon atoms arranged as hexagonal lattice, and, has high thermal conductivity and high mechanical strength.

Such graphite is widely used in an energy-storage material such as a second battery, fuel cell and supercapacitor, filter film, chemical detector, transparent electrode, and heat-dissipation material, and the like.

In particular, there is an increasing interest in the graphite sheet prepared by carbonizing the polyimide films obtained from the polyimide resin and graphitizing them.

Particularly, said graphite sheet is prepared by carbonizing and graphitizing steps, involving respective heat-treatment of polyimide films at different temperatures.

In this regard, heat applied during the carbonizing and graphitizing steps provide brittleness to the graphite sheets resulting from the polyimide films. Accordingly, the graphite sheets tend to have relative poor flexibility.

In this regard, the degradation of the flexibility can be solved by adding heat-sublimatable fillers in said polyimide film, so as to sublimate the fillers and form voids within the graphite sheet, during the carbonizing and/or graphitizing steps for preparing the graphite sheet.

However, roughness of the polyimide film surfaces may be reduced depending on factors such as an average particle diameter and contents, of the fillers. As a result, winding properties of the films may be decreased and protruding trails may be formed on the surface of the film. Further, the voids cause heat-transfer paths of the graphite sheets to be longer, resulting in problems such as a degradation of the thermal conductivity and the like.

Accordingly, in regards to the preparation of the graphite sheets, it is very difficult to simultaneously balance the excellent thermal conductivity and other physical properties of the graphite sheets.

Accordingly, there is high technical need for fundamentally solving these problems.

SUMMARY OF THE INVENTION

The present invention provides a method for preparing high-performance graphite sheet, comprising imidizing a polyamic acid resulting from a reaction of dianhydride monomer(s) and diamine monomer(s) to obtain a polyimide film, and carbonizing and/or graphitizing the polyimide film to obtain the graphite sheet;

wherein the polyimide film contains 2 or more fillers having different average particle diameters, and the thermal conductivity is at least 1,400 W/m·K.

In an embodiment of the present invention, the fillers may be sublimated at the steps of carbonizing and/or graphitizing, causing to form the voids in the graphite sheet.

Further, the fillers may comprise a first filler having a relatively large average particle diameter, and a second filler having a relatively small average particle diameter.

Meanwhile, the polyimide film may contain more than 0% to not more than 40% of the first filler, based on the total of the fillers, and at least 60% to less than 100% of the second filler, based on the total of the fillers.

In one embodiment, the first filler may have the average particle diameter of 2.0 μm to 2.5 μm, and the second filler may have the average particle diameter of 1.0 μm to 1.6 μm.

Further, the content of the fillers may be 2000 ppm to 4000 ppm based on the weight of the polyamic acid.

Meanwhile, the fillers may be at least one selected from the group consisting of calcium carbonate, calcium phosphate dibasic, and barium sulphate.

In particular, the fillers may be calcium phosphate dibasic and/or barium sulphate.

In one embodiment, heat treatment temperature of the graphitizing step may be at least 2700° C.

Further, the present invention provides a high-performance graphite sheet prepared by imidizing polyamic acid resulting from a reaction of dianhydride monomer(s) and diamine monomer(s) to obtain polyimide film, and carbonizing and/or graphitizing the polyimide film to obtain the graphite sheet;

wherein, the polyimide film contains 2 or more fillers having different average particle diameters; and the thermal conductivity is at least 1,400 W/m·K.

At this time, the polyimide film may have the average roughness (Ra) of 8 nm to 30 nm.

Further, the graphite sheet may comprise the voids formed by sublimating the fillers during the carbonizing and graphitizing steps.

At this time, at least parts of the voids may form protrusions of extruded shape on the surface of the graphite sheet.

Further, the protrusions may have an average particle diameter of less than 0.5 mm.

On the one hand, the heat treatment temperature of the graphitizing step may be at least 2700° C.

In one embodiment, said graphite sheet may have a thickness of 15 μm to 40 μm.

Further, the present invention provides the electronic device comprising the high-performance graphite sheets.

DETAILED DESCRIPTION OF THE INVENTION

Figure 1:
FIG. 1 is a photograph of an external surface of a polyimide film of comparative example 3, which is wound up.

The purpose of the present invention is to solve the problems of the conventional technologies as explained above, and technical requirement that have been requested from the past.

After careful research and various experiments, inventors of the present invention can prepare a high-performance graphite sheet having thermal conductivity of at least 1,400 W/m·K, by using polyimide films containing 2 or more fillers having different average particle diameters, as described later.

Further, in addition to the excellent thermal conductivity, since the increase of the brittleness and the degradation of the flexibility occurring from the preparation of the graphite sheet may be prevented, the excellent thermal conductivity and physical properties of the graphite sheet can be simultaneously achieved.

Further, the degradation of the processability caused by the addition of the fillers having only the small average particle diameter and the resultant decline of the roughness of the polyimide films can be prevented, and the occurrences of the protruding trails on the surface of the polyimide film can be minimized or eliminated.

Accordingly, the method according to the present invention can minimize damages, etc. occurring during the handling and molding of the graphite sheets and, therefore, can minimize or eliminate detects of the final products. Therefore, it is found that the present invention can save labor force, time and cost spent in the preparation of the graphite sheet, whereby the present invention has been accomplished.

As explained above, the method for preparing a high-performance graphite sheet according the present invention, provides the high-performance graphite sheet having a thermal conductivity of at least 1,400 W/m·K, which is prepared by using polyimides film containing 2 or more fillers having different average particle diameters.

Further, in addition to the excellent thermal conductivity, the method according to the present invention can prevent an increase of the brittleness and a degradation of flexibility which may occur during the preparation of the graphite sheet, and therefore can simultaneously achieve an excellent thermal conductivity and physical properties of the graphite sheet.

Further, the present invention can prevent the degradation of the processability due to the decline of the roughness of the polyimide films, which may results from the addition of the fillers having uniform average particle diameters, and can minimize or eliminate the occurrence of the protruding trails on the surface of the polyimide film.

Accordingly, the present invention can minimize damages, etc. may occur during the handling and molding of the graphite sheets and, therefore, can minimize or eliminate defects of the final products. Therefore, the present invention can save labor force, time and cost, spent in handling the damages and defects thereof.

The present invention will be explained in more detail below.

The present invention provides a method for preparing a high-performance graphite sheet, comprising imidizing a polyamic acid resulting from a reaction of dianhydride monomers and diamine monomers to obtain a polyimide film, and of carbonizing and/or graphitizing the polyimide film to obtain the high-performance graphite sheet; wherein the polyimide film contains 2 or more fillers having the different average particle diameters, and wherein the graphite sheet has a thermal conductivity of at least 1,400 W/m·K.

Specifically, the graphite sheet has the thermal conductivity of at least 1,500 W/m·K, more preferably at least 1,600 W/m·K.

As state above, a degradation of flexibility and an increase of brittleness of the graphite sheet may typically happen during the carbonizing and/or graphitizing steps involving the heat-treatment. In this regard, the fillers contained in the polyimide film according to the present invention may be sublimated during the carbonizing and/or graphitizing steps during the preparation of the graphite sheet, forming voids in the graphite sheet.

More concretely, the fillers are sublimated by heat during the carbonizing and/or graphitizing steps of the preparation of the graphite sheet, resulting in the gases, and the gases form explosive voids in the graphite sheet. The explosive voids formed in the graphite sheet may improve the flexibility of the graphite sheet and, as a result, improve the handling and the molding property of the graphite sheet.

Specifically, the use of 2 or more fillers having different average particle diameters in the polyimide films for the roll-type graphite sheet can simultaneously provide more excellent thermal conductivity, flexibility, and brittleness in the desired ranges during the preparation of the graphite sheet compared to the use of fillers having the uniform average particle diameter, and prevent occurrence of the protruding trails resulting from the low roughness of the surface of the polyimide film.

In particular, if the polyimide film has fillers having only small average particle diameter due to the tiny explosive voids, the thermal conductivity of the graphite sheets is maintained at least at 1,400 W/m·K and the flexibility of the sheet can be improved; whereas, due to the small average particle diameter of the fillers, the surface roughness of the polyimide films comprising the same can be declined before making the graphite sheets.

Accordingly, when the additional treatment of the polyimide films, such as corona treatment is further applied in order to improve the surface adhesion, or when the polyimide film is wound up during the preparation of the graphite sheet, the friction forces between the surfaces of the overlapping films may be increased, so that the handling property thereof may be decreased. More specifically, the increase of the friction force between the overlapping films makes it difficult to rectify the winding defects due to "obliquely tilting" occurring during the winding step of the polyimide film. Resultantly, the winding property may be decreased, and the adhesion increases during the corona treatment may cause the blocking phenomenon.

Further, if tiny foreign substances are entered between the overlapping films during the winding step, it is difficult to secure enough space to offset the size of the foreign substances. Resultantly, the repetitions of the winding step may cause thickness increase of the roll, which is responsible for the increase of the thickness deviation of the parts bearing the foreign substances. In the end, the protruding trails which are the deformations causing from the foreign substance can be formed.

Accordingly, during the preparation of the polyimide film by adding the fillers, the fillers having small average particle diameter need to be added in order to maintain the excellent thermal conductivity of the graphite sheet resulting from the polyimide film, but it may cause to reduce the surface roughness of the polyimide film, so that the product preparation processability may be degraded and the protruding trails may be formed.

On the contrary, if the polyimide film contains fillers having only the large average particle diameter, the explosive voids resulting from the sublimation of the fillers during the carbonizing and graphitizing steps, form the excessively larger protrusions, more specifically bright spots which are the protrusions having a diameter of at least about 0.5 mm on the surface of the graphite sheet, causing the external surface defects. Further, since the larger voids are responsible for the longer heat transfer path of the graphite sheet, the thermal conductivity of the graphite sheet may be reduced. As well as, the reduction of the amount of the void formed in the graphite sheet, even more, increases the brittleness of the sheet.

Consequently, by using fillers simultaneously comprising a first filler having a relatively large average particle diameter and a second filler having a relatively small average particle diameter, the graphite sheet produced therefrom may maintain the desired thermal conductivity and simultaneously may solve the problems resulting from the use of the filler having only the uniform average particle diameter.

In this regard, the dianhydride monomer may comprise at least one monomer selected from the group consisting of pyromellitic dianhydride (PMDA), biphenyltetracarboxylic dianhydride (BPDA), benzophenonetetracarboxylic dianhydride (BTDA) and oxydiphthalic anhydride (ODPA) monomers, and specifically may comprise PMDA.

Further, the diamine monomer may comprise at least one monomer selected from the group consisting of oxydianiline (ODA), methylenedianiline (MDA) and para-phenylene diamine (PPD) monomers, and specifically may comprise ODA, or ODA and MDA.

Further, the polyimide film can contain more than 0% to not more than 40% of a first filler, based on the total of the fillers, and at least 60% to less than 100% of a second filler, based on the total of the fillers.

Namely, in order to maintain the excellent thermal conductivity of the polyimide film, the second filler having the relatively small average particle diameter is contained in higher contents, compared to the first filler having the relative large average particle diameter.

Further, the first filler has the average particle diameter of 2.0 μm to 2.5 μm, and the second filler has the particle diameter of 1.0 μm to 1.6 μm.

If the compositional ratio of the first and the second fillers and/or the average particle diameters thereof are out of the range and are excessively larger or smaller, the thermal conductivity, the flexibility and the brittleness of the graphite sheet finally prepared cannot be simultaneously maintained in the desired range, and said fillers and the voids occurring during the sublimation of the fillers are responsible for the decrease of the winding property of film, the increase of the surface protruding trails, and the external surface defects of the graphite sheet, as explained above.

Meanwhile, the filler is contained in the range of 2000 ppm to 4000 ppm based on the weight of the polyamic acid.

If the filler is contained in the range of less than 2000 ppm based on the weight of the polyamic acid, the occurrence of the voids in the graphite sheet resulting from the sublimation of the fillers decreases. Resultantly, the desired flexibility increase effects may not be achieved; the surface roughness reduction of the polyimide film causes the increase of the friction force and the decrease of the winding property; and the foreign substances entered during the winding step are responsible for the protruding trails.

On the contrary, if the content of the filler is more than 4000 ppm based on the total of fillers, the occurrence of the voids in the graphite sheet due to the sublimation of the fillers excessively increases, causing the degradation of the thermal conductivity of the graphite sheet and the increase of the brittleness.

Further, 2 or more fillers having different average particle diameters may be made of the same or different materials, and specifically, the filler may be at least one selected from the group consisting of calcium carbonate, calcium phosphate dibasic, and barium sulphate.

More particularly, 2 or more fillers having different average particle diameters may be calcium phosphate dibasic and/or barium sulphate, but they are not limited thereto. If the fillers may be sublimated during the preparation of the graphite sheet involving the carbonizing and graphitizing steps of the polyimide film and may form sufficient voids, they are not significantly limited.

Further, the heat treatment temperature of the graphitizing step may be at least 2700° C.

If the heat treatment temperature of the graphitizing step is less than 2700° C., the properties involving the thermal conductivity of the graphite sheet prepared by the above process may be degraded.

Meanwhile, the present invention provides a high-performance graphite sheet prepared by imidizing the polyamic acid resulting from a reaction of dianhydride monomer(s) and diamine monomer(s) to obtain a polyimide film, and carbonizing and/or graphitizing the polyimide films; wherein, the polyimide film contains 2 or more filler having different average particle diameters; and the thermal conductivity of the graphite sheet is at least 1,400 W/m·K. More particularly, the thermal conductivity of the graphite may be at least 1,500 W/m·K, at least 1,600 W/m·K.

In this regard, the average roughness (Ra) of the polyimide film may be 8 nm to 30 nm.

If the roughness of the polyimide film is out of the above range and too low, the protruding trails occurring during winding step of the film cannot be effectively prevented and the friction force increase of the film surface causes to the decrease of the winding property, so that the manufacturing processability may be degraded.

On the contrary, if the roughness of the polyimide film is out of the above range and too high, the unnecessarily large spacing may be formed between the overlapping surfaces of the film at winding step during the processing of the polyimide films and the preparation of the graphite sheets. Further, as the repetitions of the winding step make the thickness of the roll to increase, the thickness of the roll increases too much due to the spacing, considering the thickness of the film itself, causing problems that it is not easy to handle it and that large spaces may be required for storing and transferring.

In one embodiment, the high-performance graphite sheet may comprise the voids formed by sublimating the fillers during the carbonizing and graphitizing steps.

In this regard, at least parts of the voids may form the protrusions in extrude shape on the surface of the graphite sheet, but the average particle diameter of the protrusions may be less than 0.5 mm.

The protrusion having at least 0.5 mm of the average particle diameter is referred to bright spot, and may cause the problems regarding external surface defects.

However, in the high-performance graphite sheet prepared by the method according to the present invention, the problems relating to the external surface defects can be solved by comprising the second filler having the relatively small average particle diameter in higher contents, compared to the first filler having the relative large average particle diameter.

Meanwhile, the temperature of the heat treatment of the graphitizing step may be at least 2700° C.

Further, the thickness of the graphite sheet may be 15 µm to 40 µm.

If the thickness of the graphite sheet is too thin or too thick from the desired range, the thermal conductivity of the desired range cannot be achieved and the handling and molding thereof may not be easy during the manufacturing process for applying the graphite sheet to the desired electronic device.

Further, the present invention provides an electronic device comprising a high-performance graphite sheet. In this regard, since specific types, constructions, or structures of electronic devices are known in the conventional arts, the detailed descriptions thereon will be omitted.

Although the invention will be further described through the following examples and comparative examples below, the following examples are not to be construed to limit the present invention.

EXAMPLES

Example and Comparative Example: The Preparation of the Polyimide Film

Example 1

Polyamic acid solution was prepared by adding 405.5 g of dimethylformamide as a solvent in a 0.8 L reactor; setting the temperature to 30° C.; adding and dissolving 44.3 g of ODA as diamine monomer; adding and dissolving 47.8 g of pyromellitic acid as dianhydride monomer; and polymerizing them. In the resulting polyamic acid, 0.0018 g of calcium phosphate dibasic having the average particle diameter of 2.0 µm was added as the first filler, and 0.1824 g of calcium phosphate dibasic having the average particle diameter of 1.0 µm was added as the second filler, resulting in a mixture solution wherein the content ratio of the first filler and the second filler was 1:99 and the total content of the fillers was 2000 ppm based on the weight of the polyamic acid. The resulting mixture solution was mixed with an imidization catalyst and a dehydrating agent. And then, the resultant mixture was applied on the glass plate or steel plate to the prescribed thickness (dried), and, was dried by hot-air for 4 minutes in a 110° C. oven, by hot-air for 3 minutes in a 280° C. oven, and by hot-air for 3 minutes in a 420° C. oven, to obtain the polyimide film having a thickness of 50 µm.

Example 2

The polyimide film of the example 2 was manufactured in the same manner as in example 1, with the exception that the first filler and the second filler are added in the content ratio of the first filler:the second filler of 20:80.

Example 3

The polyimide film of the example 3 was manufactured in the same manner as in example 1, with the exception that the first filler and the second filler are added in the content ratio of the first filler:the second filler of 40:60.

Example 4

The polyimide film of the example 4 was manufactured in the same manner as in example 1, with the exception that the average particle diameter of the first filler is 2.3 µm.

Example 5

The polyimide film of the example 5 was manufactured in the same manner as in example 1, with the exception that the average particle diameter of the first filler is 2.5 µm.

Example 6

The polyimide film of the example 6 was manufactured in the same manner as in example 1, with the exception that the average particle diameter of the second filler is 1.3 µm.

Example 7

The polyimide film of the example 7 was manufactured in the same manner as in example 1, with the exception that the average particle diameter of the second filler is 1.6 µm.

Example 8

The polyimide film of the example 8 was manufactured in the same manner as in example 1, with the exception that total content of the fillers is 3000 ppm based on the weight of the polyamic acid.

Example 9

The polyimide film of the example 9 was manufactured in the same manner as in example 1, with the exception that total content of the fillers is 4000 ppm based on the weight of the polyamic acid.

Example 10

The polyimide film of the example 10 was manufactured in the same manner as in example 1, with the exception that the content ratio of the first filler:the second filler is 40:60 and total content of the fillers is 3000 ppm based on the weight of the polyamic acid.

Example 11

The polyimide film of the example 11 was manufactured in the same manner as in example 1, with the exception that the content ratio of the first filler:the second filler is 40:60 and total content of the fillers is 4000 ppm based on the weight of the polyamic acid.

Comparative Example 1

The polyimide film of the comparative example 1 was manufactured in the same manner as in example 1, with the exception that only the first filler is added as a filler.

Comparative Example 2

The polyimide film of the comparative example 2 was manufactured in the same manner as in example 1, with the exception that the first filler and the second filler are added in the content ratio of first filler:second filler=45:55.

Comparative Example 3

The polyimide film of the comparative example 3 was manufactured in the same manner as in example 1, with the exception that only the second filler is added as filler.

Comparative Example 4

The polyimide film of the comparative example 4 was manufactured in the same manner as in example 1, with the exception that, instead of the first filler, a filler having an average particle diameter of 1.8 µm is added.

Comparative Example 5

The polyimide film of the comparative example 5 was manufactured in the same manner as in example 1, with the exception that, instead of the first filler, a filler having an average particle diameter of 3.0 µm is added.

Comparative Example 6

The polyimide film of the comparative example 6 was manufactured in the same manner as in example 1, with the exception that, instead of the second filler, a filler having an average particle diameter of 0.5 µm is added.

Comparative Example 7

The polyimide film of the comparative example 7 was manufactured in the same manner as in example 1, with the exception that, instead of the second filler, a filler having an average particle diameter of 1.8 µm is added.

Comparative Example 8

The polyimide film of the comparative example 8 was manufactured in the same manner as in example 1, with the exception that total content of the fillers is 1000 ppm based on the weight of the polyamic acid.

Comparative Example 9

The polyimide film of the comparative example 9 was manufactured in the same manner as in example 1, with the exception that total content of the fillers is 5000 ppm based on the weight of the polyamic acid.

Experimental Example 1

The polyimide films, prepared in example 1 to example 9 and comparative example 1 to comparative example 9, were scaled up to obtain the polyimide films having a length of 100 m. The average roughness and the number of occurrence of the protruding trails, of the polyimide films prepared as above, were measured and shown in table 1 below.

For reference, said average roughness were measured according to ISO 1997 method (Cut off: 0.25 mm, measurement speed: 0.1 mm/sec, measurement length per 1 time: 3 mm). Five measurements were taken and the average value obtained therefrom was used. In this regard, the average roughness was measured on the air surface of the polyimide films.

Further, the numbers of the occurrence of the protruding trails were measured by counting the numbers of the protruding trails occurring on the outmost surface of the rolls after 100 m of the polyimide films were wound as a roll and before the respective graphite sheets are prepared therefrom.

TABLE 1

| Example No. | Average roughness (nm) | Numbers of the protruding trail (EA) |
| --- | --- | --- |
| example 1 | 8.1 | 1 |
| example 2 | 11.4 | 0 |
| example 3 | 14.6 | 0 |
| example 4 | 8.2 | 0 |
| example 5 | 8.4 | 1 |
| example 6 | 13.1 | 0 |
| example 7 | 18.1 | 0 |
| example 8 | 11.3 | 1 |
| example 9 | 15.7 | 0 |
| example 10 | 20.9 | 0 |
| example 11 | 27.7 | 0 |
| comparative example 1 | 24.1 | 0 |
| comparative example 2 | 15.4 | 0 |
| comparative example 3 | 7.6 | 7 |
| comparative example 4 | 20.5 | 0 |
| comparative example 5 | 8.3 | 1 |
| comparative example 6 | 4.7 | 12 |
| comparative example 7 | 20.9 | 0 |
| comparative example 8 | 5.3 | 16 |
| comparative example 9 | 18.4 | 0 |

Experimental Example 2

In the carbonizing step, respective polyimide films prepared by scaling up in the above experimental example 1, were heated to 1200° C. at a rate of 3° C./minute under a nitrogen atmosphere in the high temperature furnace, and maintained for about 2 hours. Then, in the graphitizing step, the resultant materials were heated to 2800° C. at a rate of 5° C./minutes under the argon gas in the very high temperature furnace and maintained for 1 hour, followed by cooling to obtain the graphite sheet having a thickness of 25 µm.

The thermal conductivity, the brittleness, and the numbers of occurrence of the bright spots of the prepared graphite sheet above were measured and shown in the table 2 below.

For reference, the thermal conductivity was measured according to ASTM E 1461 method which is a standard measurement for the thermal conductivity of the heat-dissipation material. Further, the brittleness of the materials respectively obtained in examples and comparative examples was verified using the folding endurance measurement.

In this regard, the folding endurance was measured by repeatedly folding and unfolding the graphite sheets prepared from the polyimide films of the examples and the comparative examples, and measuring the number of repetition until the graphite sheets were cut off. The folding endurance was measured using MIT-DA (Folding Endurance Tester, manufacturer: TOYOSEIKY). Graphite sheets were cut to a width of 15 mm, and were measured under the following conditions: radius of curvature of the clamp for holding and folding the graphite sheet: 0.5 mm; folding angle: 135° folding rate: 90 times/minute; loading: 250 g.

For reference, the higher the brittleness of the graphite sheet, the less the number of repetitions until cut. In contrast, the lower brittleness is verified by the more number of repetitions until cut.

Further, the number of occurrence of the bright spots is a parameter showing the occurrence of the surface defects of the graphite sheet, and is measured by counting the number of occurrence of the protrusions having a size of at least 0.5 mm within the square of 100 mm×100 mm.

TABLE 2

| Example No. | Thermal conductivity (W/m · K) | Folding endurance Number of repetition | Number of occurrence of bright spot (EA) |
| --- | --- | --- | --- |
| example 1 | 1598 | 22 | 0 |
| example 2 | 1550 | 18 | 0 |
| example 3 | 1533 | 15 | 0 |
| example 4 | 1597 | 16 | 0 |
| example 5 | 1559 | 13 | 0 |
| example 6 | 1523 | 19 | 0 |
| example 7 | 1509 | 16 | 0 |
| example 8 | 1566 | 25 | 0 |
| example 9 | 1519 | 33 | 0 |
| example 10 | 1518 | 24 | 0 |
| example 11 | 1502 | 30 | 0 |
| comparative example 1 | 1394 | 5 | 3 |
| comparative example 2 | 1488 | 14 | 3 |
| comparative example 3 | 1586 | 23 | 0 |
| comparative example 4 | 1433 | 16 | 2 |
| comparative example 5 | 1480 | 7 | 5 |
| comparative example 6 | 1683 | 17 | 0 |
| comparative example 7 | 1443 | 9 | 1 |
| comparative example 8 | 1598 | 3 | 0 |
| comparative example 9 | 1461 | 30 | 4 |

As shown in tables 1 and 2 above, it was confirmed that the graphite sheets prepared from the polyimide films of examples 1 to 9 fulfilling the content ratio, the particle diameter and the total content requirement according to present invention, can simultaneously maintain an excellent thermal conductivity, flexibility and lower brittleness, compared to the graphite sheets prepared from the polyimide films of the comparative examples 1 to 9 which do not fulfill at least one requirement selected from the content ratio, the particle diameter, and total content of the filler; and that the addition of the fillers having different average particle diameters in the desired range, can prevent the occurrence of the protruding trails on the film surface resulting from the entrance of the foreign substances during winding the polyimide films and no bright spot resulting from the sublimation of the fillers was found in the graphite sheet according to present invention.

On the contrary, the graphite sheets of comparative example 3 (containing only the second filler), comparative example 6 (containing the filler having the smaller average particle diameter than the second filler), and comparative example 8 (the total content of the fillers is too low out of the desired range), exhibited excellent thermal conductivity, compared to those of other comparative examples, but, it is shown that because of the low roughness of the polyimide films, the decrease of the winding property happened during the treatment procedures and the protruding trails resulting from the entrance of the foreign substances during the winding of the film were formed on the surface thereof.

Further, regarding the graphite sheets of comparative example 1 (containing only the first filler having the relatively large average particle diameter), comparative example 2 (the content ratio of the first filler having a relatively large average particle diameter, is higher), comparative example 4 (containing the filler having smaller average particle diameter than the first filler), comparative example 5 (containing the filler having larger average particle diameter than the first filler), comparative example 7 (containing the filler having larger average particle diameter than the second filler), and comparative example 9 (the total content of the fillers is too high and out of the desired range), it was shown that the roughness thereof were higher than those from the other comparative examples, but the thermal conductivities thereof declined due to the variation of the amounts and the distributions of the voids in the graphite sheet and that the bright spots occurred on the surface of the graphite sheet.

Especially, in regards to comparative example 1 (containing only the first filler having a relatively large average particle diameter), comparative example 5 (containing the filler having the larger average particle diameter than the first filler), comparative example 7 (containing the filler having the larger average particle diameter than the second filler), and comparative example 8 (the total content of the fillers is too low out of the desired range), it is confirmed that the reduction of the absolute amount of filler particles tends to increase the brittleness thereto.

FIG. 1 shows a photograph of the external surface taken during winding of the polyimide film of comparative example 3.

In view of FIG. 1, during winding of the polyimide film of comparative example 3 containing only the second filler having relatively small average particle diameter, the refraction of the image reflected on the surface shows that the entrance of the foreign substances between the overlapping films is responsible for the protruding trails marked by the red circle.

Figure 2:
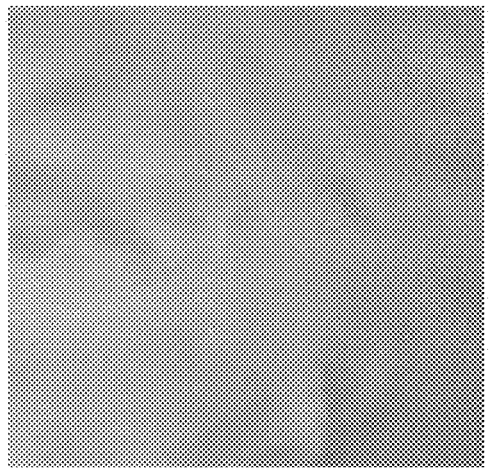
FIG. 2 is a photograph of an external surface of a graphite sheet prepared from a polyimide film of example 1.
Figure 3:
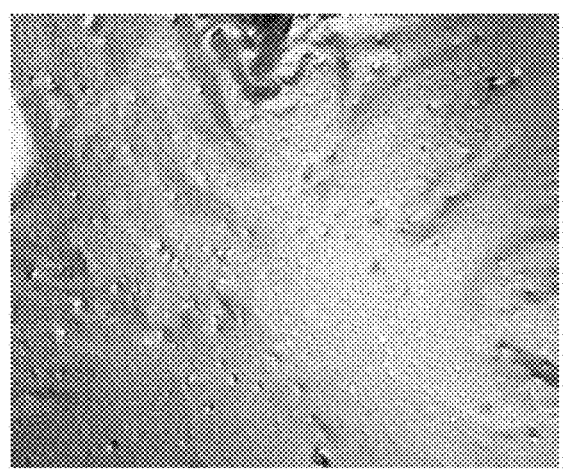
FIG. 3 is a photograph of an external surface of a graphite sheet prepared from a polyimide film of comparative example 1.

FIG. 2 and FIG. 3 respectively show photographs of an external surface of a graphite sheets prepared from a polyimide film of the example 1 and the comparative example 1.

FIG. 2 and FIG. 3 show that the external surface of the graphite sheet prepared from the polyimide film of example 1, which fulfills the requirements of the particle diameter, content ratio and total content, is smooth.

On the contrary, in the graphite sheet prepared from the polyimide film of comparative example 1 comprising only the first filler having the relative large average particle diameter as filler, the bright spots resulting from the large voids were formed, which is responsible for the occurrence of the external surface defects.

While the present invention was shown and described with reference to exemplary embodiments and drawings thereof, it will be understood by those skilled in the art that various changes and modifications may be made therein without departing from the scope of the invention as defined by the appended claims.

What is claimed is:

1. A polyimide film for preparing a graphite sheet, the polyimide film comprising:
   a first filler having an average particle diameter of 2.0 µm to 2.5 µm, and
   a second filler having an average particle diameter of 1.0 µm to 1.6 µm, wherein the first filler or the second filler is at least one selected from the group consisting of calcium carbonate, calcium phosphate dibasic, and barium sulphate, wherein the polyimide film is formed by imidizing a polyamic acid; and wherein the first and second fillers have a total content of 2000 ppm to 4000 ppm based on the weight of the polyamic acid, and wherein the thermal conductivity of the graphite sheet is at least 1,400 W/m·K.

2. The polyimide film for preparing a graphite sheet according to claim 1, wherein the first and second fillers are sublimated during carbonizing and/or graphitizing step, forming voids in the graphite sheet.

3. The polyimide film for preparing a graphite sheet according to claim 2, wherein at least parts of the voids form protrusions of extruded shape on the surface of the graphite sheet.

4. The polyimide film for preparing a graphite sheet according to claim 3, wherein the protrusions have an average particle diameter of less than 0.5 mm.

5. The polyimide film for preparing a graphite sheet according to claim 2, wherein the graphitizing step is carried out at a temperature of at least 2700° C.

6. The polyimide film for preparing a graphite sheet according to claim 1, wherein the first or the second fillers are calcium phosphate dibasic and/or barium sulphate.

7. The polyimide film for preparing a graphite sheet according to claim 1, wherein the polyimide film has an average roughness (Ra) of 8 nm to 30 nm.

8. The polyimide film for preparing a graphite sheet according to claim 1, wherein the polyimide film contains more than 0% to not more than 40% of the first filler, and at least 60% to less than 100% of the second filler, based on the total of the first and second fillers.

9. The polyimide film for preparing a graphite sheet according to claim 1, wherein the graphite sheet has a thickness of 15 μm to 40 μm.

* * * * *